(12) United States Patent
Hua et al.

(10) Patent No.: US 9,802,962 B2
(45) Date of Patent: Oct. 31, 2017

(54) TRICYCLIC PYRONE COMPOUNDS REDUCE AMYLOID BETA AGGREGATES

(71) Applicants: AfaSci, Inc., Redwood City, CA (US); Kansas State University Research Foundation, Manhattan, KS (US); The Regents of the University of California, Oakland, CA (US)

(72) Inventors: Duy H Hua, Manhattan, KS (US); Lee-way Jin, Davis, CA (US); Izumi Maezawa, Sacramento, CA (US); Xinmin Xie, Burlingame, CA (US)

(73) Assignees: KANSAS STATE UNIVERSITY RESEARCH FOUNDATION, Manhattan, KS (US); THE REGENTS OF THE UNIVERSITY OF CALIFORNIA, A CALIFORNIA CORPORATION, Oakland, CA (US); AFASCI, INC., Redwood City, CA (US)

(*) Notice: Subject to any disclaimer, the term of this patent is extended or adjusted under 35 U.S.C. 154(b) by 13 days.

(21) Appl. No.: 14/503,262

(22) Filed: Sep. 30, 2014

(65) Prior Publication Data

US 2015/0119406 A1    Apr. 30, 2015

Related U.S. Application Data

(60) Provisional application No. 61/884,449, filed on Sep. 30, 2013.

(51) Int. Cl.
*C07D 519/00* (2006.01)
*C07D 493/04* (2006.01)

(52) U.S. Cl.
CPC ......... *C07D 519/00* (2013.01); *C07D 493/04* (2013.01)

(58) Field of Classification Search
CPC .................... C07D 519/00; C07D 493/04
See application file for complete search history.

(56) References Cited

U.S. PATENT DOCUMENTS

| 3,558,658 A | 1/1971 | McIntyre |
| 6,384,045 B1 | 5/2002 | Hua et al. |
| 7,935,726 B1 * | 5/2011 | Hua .............................. 514/455 |

OTHER PUBLICATIONS

Alzheimers Association, Experimenal Alzheimer drugs Targeting Beta-Amyloid and the "Amyloid Hypothesis", 2008, www.alz.org.*
Pokhrel et al., Caplus an 2012:1431441, 2012.*
Pokhrel et al., Caplus an 2012:561690, 2012.*
Pokhrel et al.-2, Bioorganic & Medicinal Chemistry Letters, 22, 2012, 3480-3484.*
Rana et al., "Synthesis of tricyclic pyrones and pyridinones and protection of Aβ-peptide induced MC65 neuronal cell death," Bioorganic & Medicinal Chemistry Letters vol. 19 (2009), pp. 670-674.
Pokhrel et al., "Inhibition of Acyl-CoA: Cholesterol Acyltransferase (ACAT), Overexpression of Cholesterol Transporter Gene, and Protection of Amyloid β (Aβ) Oligomers-Induced Neuronal Cell Death by Tricyclic Pyrone Molecules," Journal of Medical Chemistry (2012), pp. 8969-8973, American Chemical Society.

* cited by examiner

*Primary Examiner* — Sun Jae Yoo
(74) *Attorney, Agent, or Firm* — Morgan, Lewis & Bockius LLP

(57) ABSTRACT

Tricyclic pyrone compounds having high oral bioavailability, excellent blood-brain barrier permeability, and low toxicity are presented. Administration of the compounds to Alzheimer's Disease transgenic models resulted in substantially reduced soluble and insoluble Aβ species in the brain without affecting general behavior and motor coordination. Furthermore, in addition to blocking the toxicity and formation of both intraneuronal and extracellular Aβ aggregates, the compounds also increase cellular cholesterol efflux, restore axonal trafficking, and enhance hippocampal synaptic plasticity.

7 Claims, 17 Drawing Sheets

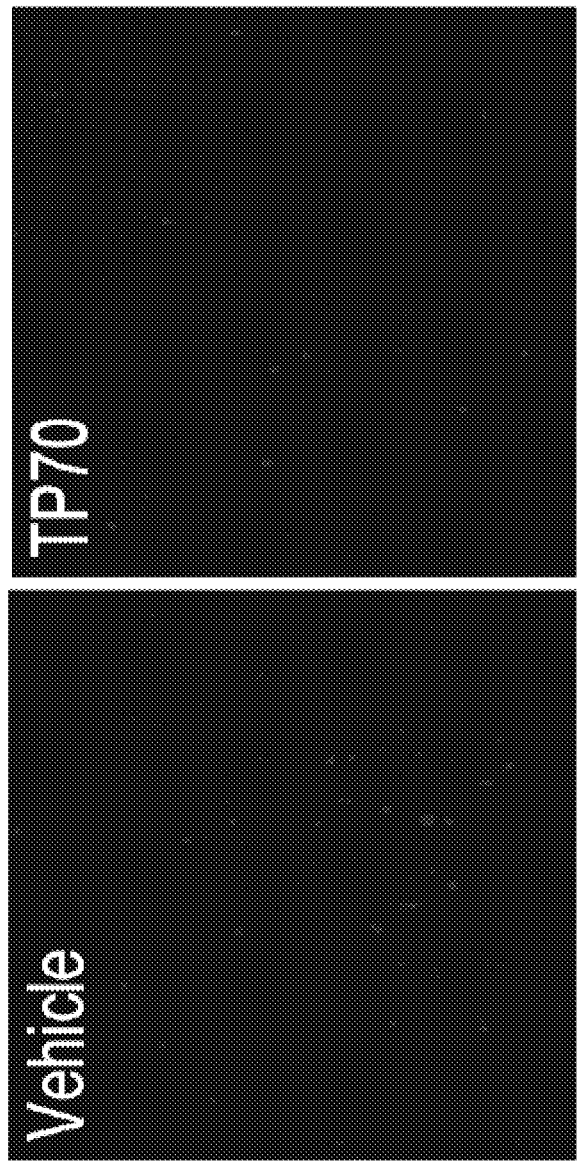

TRICYCLIC PYRONE COMPOUNDS REDUCE AMYLOID BETA AGGREGATES

CROSS-REFERENCE TO RELATED APPLICATIONS

This application claims the benefit of U.S. Provisional Application Ser. No. 61/884,449, filed Sep. 30, 2013, which is incorporated herein by reference in its entirety.

SPONSORED RESEARCH OR DEVELOPMENT

This invention was made with U.S. Government support under Grant Numbers R01 AG025500 and R43 AG43203 awarded by National Institutes of Health. The U.S. Government has certain rights in this invention.

BACKGROUND OF THE INVENTION

Alzheimer's disease (AD) afflicts approximately 35 million people worldwide and is the most common cause of dementia in the elderly. There is an unmet medical need for new AD therapeutic development. Amyloid-beta (Abeta or Aβ) deposited in AD brains has been hypothesized to initiate a cascade of molecular changes leading to synaptic dysfunction, inflammation, and neuronal death observed in AD brains. Therefore, designing therapies targeting Abeta and downstream events has become a major effort in AD drug development. We have synthesized a class of tricyclic pyrone compounds (TPs). The lead compounds were found to have high oral bioavailability, excellent blood-brain barrier permeability, and low toxicity. Administering the compounds either orally or intraperitoneally to young AD transgenic models in 'preventive studies' resulted in substantially reduced soluble and insoluble Abeta species in the brain and preserved memory and motor function. Furthermore, we have found that in addition to being able to block the toxicity and formation of both intraneuronal and extracellular Aβ aggregates, the lead TPs also increase cellular cholesterol efflux, restore axonal trafficking, and enhance hippocampal synaptic placidity—these synergistic cellular actions could be potential mechanisms underlying in vivo effects.

As populations worldwide age and the number of subjects with Alzheimer's continues to expand, effective treatments are being actively pursued. To date, however, only a limited number of pharmacological agents heretofore have been identified as effective in treating symptoms of AD in a person suffering therefrom. The most prominent of these today are tacrine and donepezil hydrochloride, which are cholinesterase inhibitors active in the brain. Thus, there is a need in the art for additional therapeutic agents for treating Alzheimer's and other neurodegenerative disorders.

BRIEF SUMMARY OF THE INVENTION

One embodiment of this invention comprises a tricylic pyrone selected from the compounds having the formulae provided in FIG. 1 and FIG. 7. One embodiment of the invention comprises a tricylic pyrone compound selected from the compounds numbered TP4, TP36, TP54, TP70, TP82 and TP101 as provided in FIG. 1. One embodiment of the invention is compound TP70 (formula provided in FIG. 1). One embodiment of the invention comprises a method of treating a patient with AD, said method comprising administering one or more TP compounds to said patient. One embodiment of the invention comprises a method of reducing soluble and/or insoluble Aβ species in the brain, said method comprising administering an effective dose of one or more TP compounds to a human. In one embodiment of the invention, the TP compound is co-administered with a molecule other than a TP compound.

Additional embodiments, objects and advantages of the present invention are apparent from the detailed description set forth below.

BRIEF DESCRIPTION OF THE DRAWINGS

FIG. 2A. Top panels show superimposed field excitatory post-synaptic potentials (EPSPs) taken from baseline and 45 min following high frequency stimulation (HFS, four 1-s trains of 100 pulses of 0.2 ms delivered at 100 Hz, inter-train interval of 20 s) of the Schaffer collateral-CA1 synapses. FIG. 2B. Lower panel shows the plot that each field EPSP slope was normalized to that just prior to the HFS and plotted as a function of recording time. In Control HFS induced LTP. AβO blocked LTP. TP70 (1 µM) restored LTP in the presence of AβO. TP70 alone enhanced LTP.

FIG. 3A. CP2 and TP70 plasma and brain concentrations following i.v. injection in mice (n=3). FIG. 3B. Plasma drug concentration kinetics is fitted with a 3-compartment model with an elimination t½ of 2.5 h and slow redistribution from peripheral tissues into plasma. The drug concentration was determined using HPLC and mass spectrometry.

FIGS. 6A-6E. 2-month-old 5×FAD mice were treated with TP70 or vehicle for 6 weeks as described in the text. Four cortical sections evenly distributed through the cerebrum were taken from one hemisphere of each mouse (6 mice in each treatment group) and fluorescently stained with the amyloid dye FSB (blue) and the nuclear dye propidium iodide (PI, red). A: Representative sections that show the PI stain. B: Representative sections that only show the FSB stain. C: Fluorescent staining was objectively quantified by LSC. LSC histograms show no difference in nuclear count (PI stain) in sections between groups and a substantial reduction of plaque count (FSB stain) in the TP70 treated group (red tracing) compared to the vehicle-treated group (blue tracing). D: LSC quantification showed a significant difference between the two groups; n=6, p<0.001. E: A representative Western blot containing the soluble fractions of three mice of each group was analyzed for soluble Aβ dimer (see ref 59 for the method).

DETAILED DESCRIPTION OF THE INVENTION

I. Introduction

Figure 1:
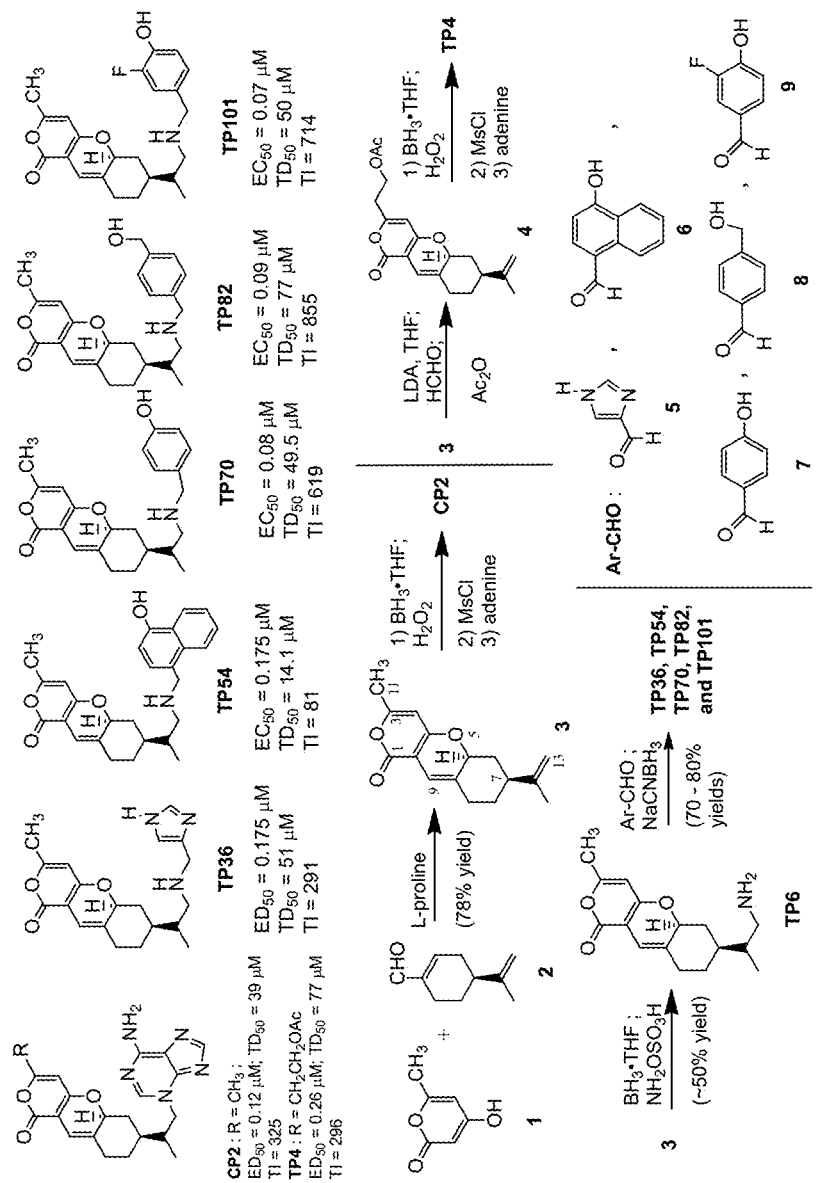
FIG. 1. One embodiment of the invention comprises a tricylic pyrone compound selected from the compounds numbered TP4, TP36, TP54, TP70, TP82 and TP101. One embodiment of the invention is compound TP70.

Following the widely accepted amyloid cascade hypothesis, a large percentage of current therapeutic development in AD is focused on those targeting Aβ peptide or Aβ aggregates. Many forms of Abeta aggregates are toxic and have been shown to cause impaired synaptic plasticity and memory in animal models. The most toxic species appear to be the intraneuronally accumulated Abeta and soluble extracellular Abeta-Oligomers (AβO) including low-n-oligomers such as the Abeta dimer and high-n-oligomers such as the 12 mer Abeta*56. Agents that reduce Abeta production, such as beta- and gamma-secretase inhibitors; agents that increase Abeta clearance, such as amyloid vaccines; and agents that block Abeta aggregation, such as non-steroidal anti-inflammatory agents, as well as antioxidants and inhibitors of tau protein phosphorylation have been investigated. Many compounds have shown efficacy in AD transgenic mouse models, but their efficacy in AD patients remains uncertain, and recently several drug candidates in clinical trials failed to show benefits.

We have designed and synthesized molecules that can slow or halt the disease process, and reduce cognitive impairment. Although the exact molecular targets and mechanisms of action of TPs await further investigation, at least several complementary mechanisms may contribute to their beneficial effects: (1) TPs directly interact with Aβ to block their toxicity and reverse their aggregation; (2) TPs inhibit acyl-coenzyme A: cholesterol acyltransferase (ACAT), thereby modulating cholesterol pathways in neurons, which may slow down AD progression; (3) TPs restore axonal trafficking of mitochondria in neurons, and enhance hippocampal synaptic plasticity.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are intended to be defined as indicated below.

Definitions

"Compound of the invention," as used herein refers to the compounds discussed herein, salts (e.g. pharmaceutically acceptable salts), prodrugs, solvates and hydrates of these compounds.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

"Moiety" refers to a radical of a molecule that is attached to the remainder of the molecule.

The symbol ⁓, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR''''—C(NR'R"R''')=NR'''', —NR"—C(NR'R") =NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

The term "prevention" refers to the use for reducing the occurrence of the disease.

Heteroatoms include oxygen (O), nitrogen (N) sulfur (S), silicon (Si), germanium (Ge), aluminum (Al) and boron (B).

By "effective" amount of a drug, formulation, or permeant is meant a sufficient amount of an active agent to provide the desired local or systemic effect.

The term "pharmaceutically acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the present invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

By the term "neurodegenerative disease" is meant any pathological state involving neuronal degeneration, including Parkinson's Disease, Huntington's Disease, Alzheimer's Disease, and amyotrophic lateral sclerosis (ALS).

As used herein the term "Alzheimer's disease" (AD) encompasses all forms of the disease, including sporadic AD, ApoE4-related AD, other mutant APP forms of AD (e.g., mutations at APP717, which are the most common APP mutations), mutant PS1 forms of familial AD (FAD) (see, WO 96/34099), mutant PS2 forms of FAD (see, WO 97/27296), and alpha-2-macroglobulin-polymorphism-related AD.

The Embodiments
The Compounds

In various embodiments, the invention provides compounds of use in treating neurodegenerative disease. In an exemplary embodiment, the compound of the invention has the formula:

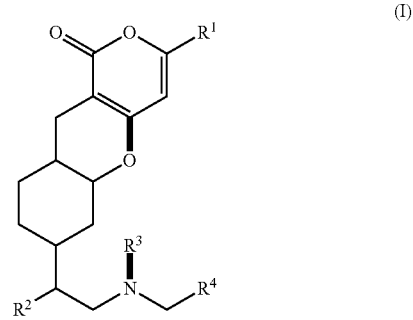

in which $R^1$, $R^2$, and $R^3$ are independently selected from substituted or unsubstituted alkyl or substituted or unsubstituted heteroalkyl. $R^4$ is substituted or unsubstituted aryl or substituted or unsubstituted heteroaryl.

In various embodiments, the invention provides a compound having the formula:

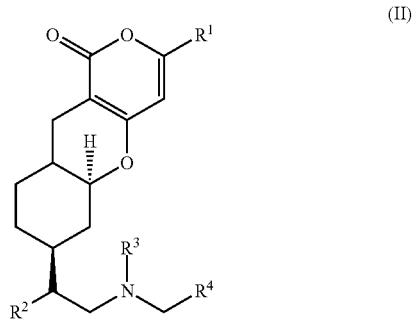

In various embodiments, the invention provides a compound according to Formula III:

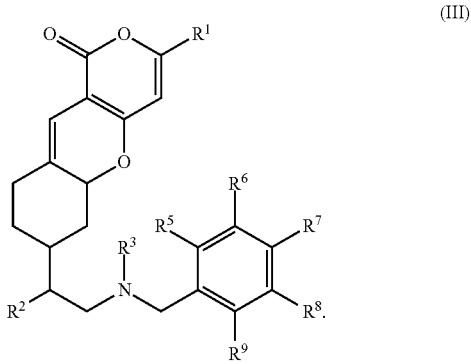

In an exemplary embodiment, the invention provides a compound having the structure according to Formula IV:

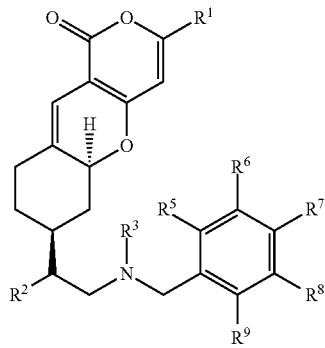

(IV)

in each for Formulae III and IV, $R^1$, $R^2$, and $R^3$ are as discussed above. $R^5$, $R^6$, $R^7$, $R^8$, and $R^9$ are independently selected from H, substituted or unsubstituted alkyl, substituted or unsubstituted heteroalkyl, substituted or unsubstituted aryl, substituted or unsubstituted heteroaryl, halogen, $BR^7R^8$, CN, $CF_3$, acyl, $-SO_2NR^{10}R^{11}$, $-NR^{10}R^{11}$, $-OR^{10}$, $-S(O)_2R^{10}$, $-C(O)R^{10}$, $-COOR^{10}$, $-CONR^{10}R^{11}$, $-S(O)_2OR^{10}$, $-OC(O)R^{10}$, $-C(O)NR^{10}R^{11}$, $-NR^{10}C(O)R^{11}$, $-NR^{10}SO_2R^{11}$ and $-NO_2$. Optionally, two or more of $R^5$, $R^6$, $R^7$, $R^8$, and $R^9$, together with the atoms to which they are bonded, are joined to form a ring system which is a member selected from substituted or unsubstituted cycloalkyl, substituted or unsubstituted heterocycloalkyl, substituted or unsubstituted aryl and substituted or unsubstituted heteroaryl.

$R^{10}$ and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. Optionally, $R^{10}$ and $R^{11}$, together with the atoms to which they are bonded, are joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

In an exemplary embodiment, at least one of $R^5$, $R^6$, $R^7$, $R^8$, and $R^9$ is selected from OH, $C_1$-$C_6$ alkoxy, $C_1$-$C_6$ hydroxyalkyl and a combination thereof.

In an exemplary embodiment, according to Formulae III and IV, one or more of $R^5$ and $R^6$; $R^6$ and $R^7$; $R^7$ and $R^8$, or $R^8$ and $R^9$, together with the atoms to which they are bonded, are joined to form a phenyl ring, such that the aryl moiety is substituted or unsubstituted napthyl. In an exemplary embodiment, according to Formulae III and IV, the aryl moiety is napthyl substituted with a member selected from OH, $C_1$-$C_6$ alkoxy, $C_1$-$C_6$ hydroxyalkyl and a combination thereof.

In an exemplary embodiment, $R^4$ is other than:

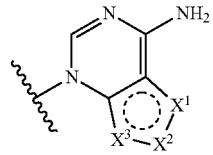

in which $R^5$ and $R^6$ are joined to form a five-member or six-member ring having two nitrogens.

In an exemplary embodiment, $R^4$ is other than:

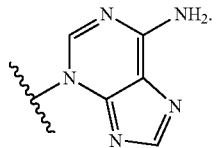

in which $X^1$, $X^2$ and $X^3$ are independently selected from N, NH, and CH, with the proviso that at least two of $X^1$, $X^2$ and $X^3$ are N or NH.

In an exemplary embodiment, $R^4$ is other than adenine. In an exemplary embodiment, $R^4$ is other than adenine bonded to the remainder of the molecule through an endocyclic nitrogen.

In various embodiments, $R^4$ is other than:

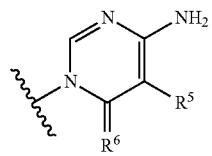

In various embodiments, the compound of the invention is a compound of FIG. 1, identified therein as TP36, TP54, TP70, TP82 and TP101.

Pharmaceutical Formulations

In another aspect, the invention is a pharmaceutical formulation, e.g., one intended for use in the treatment or prevention of a neurodegenerative disease (e.g., Alzheimer's disease). Exemplary pharmaceutical formulations of the invention include: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (*Journal of Chromatography B* (1996) volume 677, pages 1-27).

Compound half-life is inversely proportional to the frequency of dosage of a compound. In vitro half-lives of compounds may be predicted from assays of microsomal half-life as described by Kuhnz and Gieschen (*Drug Metabolism and Disposition*, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat*. B677: 1-27). Compound half-life is inversely proportional to the frequency of dosage of a compound. In vitro half-lives of compounds may be predicted from assays of microsomal half-life as described by Kuhnz and Gleschen (*Drug Metabolism and Disposition*, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

Administration

In various embodiments, the invention provides a method of treating or preventing a neurodegenerative disease in a subject in need thereof. The method includes administering an amount of a compound of the invention sufficient to provide a prophylatic or therapeutic effect. Exemplary neurodegenerative diseases treatable by a method of the invention include Alzheimer's disease and cognitive impairment, e.g., mild cognitive impairment ("MCI").

For any compound used in the method of the invention to treat or prevent a neurodegenerative disease, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture. Such information can be used to more accurately determine useful doses in humans.

In general, the compounds prepared by the methods, and from the intermediates, described herein will be administered in a therapeutically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain therapeutic effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m²/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

In an exemplary embodiment, the invention provides a combination comprising the compound according to any of the above paragraphs, together with at least one other therapeutically active agent.

In an exemplary embodiment, the invention provides a pharmaceutical composition comprising the compound according to any of the above paragraphs, and a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

EXAMPLES

The following Examples illustrate the synthesis of representative compounds used in the present invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Example 1

Synthesis of TP Compounds

Using a rational design approach, we have designed and synthesized TP compounds. The TP core structure, represented by compound 3 (FIG. 1), was prepared in one step from the condensation of 4-hydroxy-6-methyl-2-pyrone (1) and (S)-(−)-perillaldehyde (2) (Hua, et al., *Journal of Organic Chemistry*, 1997, 62:6888-6896). Selective hydroboration of the C12,13 double bond of 3 with borane followed by $H_2O_2$, mesylation with methanesulfonyl chloride, and displacement with adenine afforded CP2 (Hua, et al., *Tetrahedron*, 2003, 59:4795-4803). The C3 methyl group of compound 3 can be selectively alkylated to provide TP4 (Trushina, et al., *BMC Neurosci*, 2009, 10:73). Analogs TP36, TP54, TP70, TP82, and TP101 were synthesized from reductive amination reactions of aryl carboxaldehydes [Ar-CHO; i.e., compound 5, 6, 7, 8, and 9, respectively] and TP6 (derived from a selective amination of compound 3 with borane and hydroxylamine-O-sulfonic acid) followed by NaCNBH$_3$. Hence, these five hits can readily be synthesized from commercially available starting materials 1, 2, and aryl carboxaldehydes 5-9, respectively, in three simple steps in good yields. An advantage for the scale-up of the TP series is the high synthetic tractability of this compound class.

Example 2

Discovery of Novel Analogs of CP2 and In Vitro Profiling of TP70

Employing medium-throughput cell-based MC65 protection assay to screen over one hundred TP compounds, seven TP compounds that protect MC65 neuroblastoma cells from death caused by intracellular Aβ have been identified. The confirmed hits TP4, TP36, TP54, TP70 (compound 2b in FIG. 7), TP82 (compound 2e in FIGS. 7), and TP101 (compound 3f in FIG. 7) are novel analogs of CP2 (FIG. 1) with effective concentrations for 50% cell survival (EC$_{50}$) values in the nanomolar range. The EC$_{50}$ values for CP2, TP70, and TP101 are 120, 80, and 70 nM, respectively. The remaining TP analogs have EC$_{50}$ ranging from 0.2 to 10 μM and some TPs, e.g., TP49 (structure not shown) are inactive.

Cerep, Inc., was contracted to profile the preferred embodiment, TP70 on protein binding, in vitro absorption (using Caco-2 and P-gp efflux inhibition), in vitro metabolic stability (using human liver microsomes), and common "off target activity" including inhibitions of the cytochrome P450 superfamily (CYP1A2, CYP2B6, CYP2C8, CYP2C9, CYP2C19, CYP2D6, CYP2E1, CYP3A4, and CYP3A5), cell viability (HepG2 cells), and predictive cardiac toxicity (hERG K+ channels), and found that the compound has druggable profiles better or similar to several currently used drugs or reference compounds (e.g. simvastatin, quinidine, warfarin, labetalol, propranolol, verapanmil, quercetin, and chlorpromazine).

Example 3

Mechanistic Studies on TP70, Especially on Rat Hippocampal Long-Term Potentiation CP2 and TP70 were found to inhibit ACAT with a half maximal inhibitory concentration (IC$_{50}$) of 1.2 and 0.3 μM, respectively and increase ABCA1 cholesterol transporter gene with EC$_{50}$ values of 0.9 and 1.1 μM, respectively. It has been reported that an induction of cholesterol efflux resulting in a reduction of Aβ formation/deposition in vitro and in vivo (Kim, et al., *J Alzheimers Dis,* 2009, 16:121-131). For additional Detail, see the attached manuscript entitled, "Inhibition of Acyl-CoA: Cholesterol Acyltransferase (ACAT), Overexpression of Cholesterol Transporter Gene, and Protection of Amyloid β (Aβ) Oligomers-Induced Neuronal Cell Death by Tricylic Pyrone Molecules" which is incorporated herein.

Figure 2A:
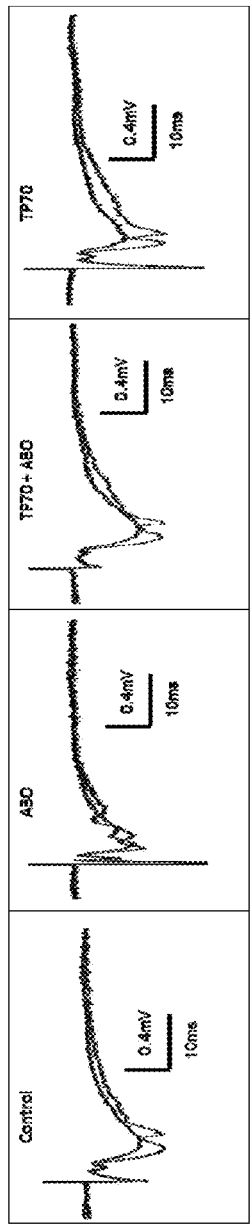
FIGS. 2A-2B. Effects of TP70 on rat hippocampal LTP.
Figure 2B:
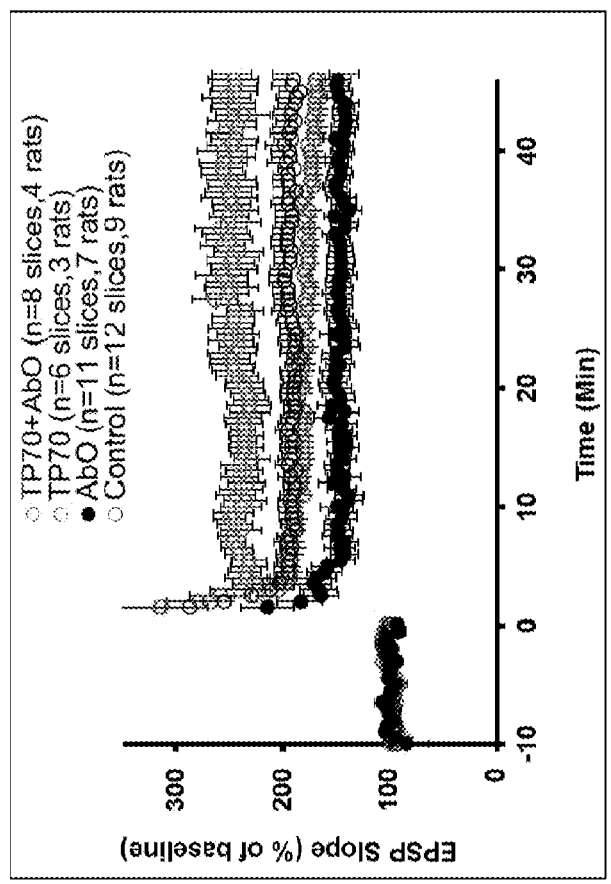

We further investigated effects of TP70 on basal neurotransmission and synaptic plasticity, for example long-term potentiation (LTP) in rat hippocampal slices as previously described (Villeda, et al., *Nature,* 2011, 477:90-94; Xie, et al., *Pflugers Arch,* 1994, 427:481-486). We demonstrated that (AβO) blocked LTP induction at 50-100 nM. TP70 (1 μM) perfused for 20 min prior to co-application of AβO restored LTP to the non-AβO-treated level. Interestingly, TP70 alone also significantly enhanced the magnitude of LTP without affecting basal synaptic activity (FIG. 2). The inactive analog TP49 had no effects. These results suggest that TP70 can block AβO-induced toxicity and preserve hippocampal synaptic plasticity. TP compounds appear to possess multiple beneficial effects.

Example 4

In Vivo PK Studies of TP70

Figure 3A:
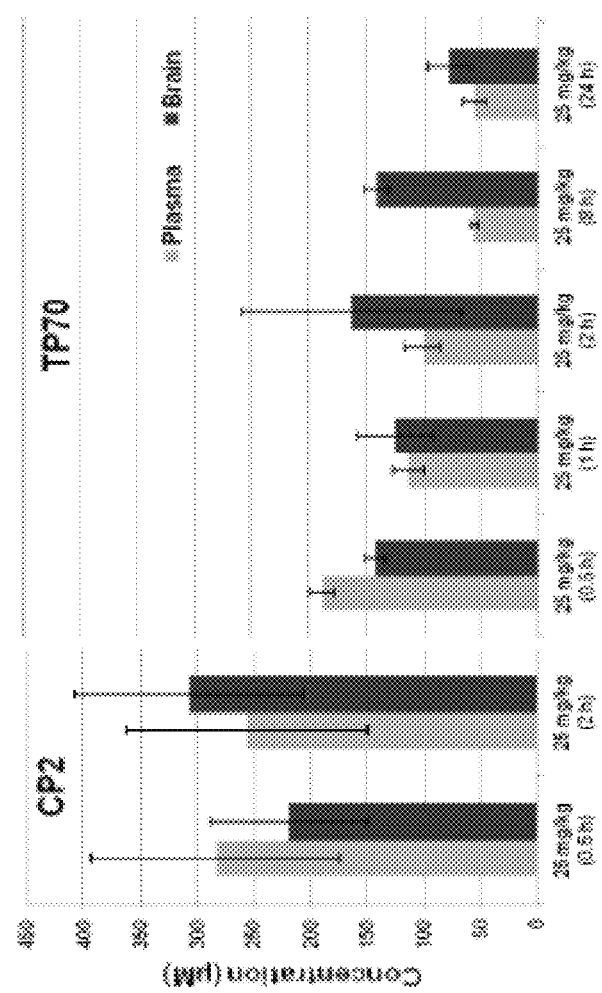
FIGS. 3A-3B.
Figure 3B:
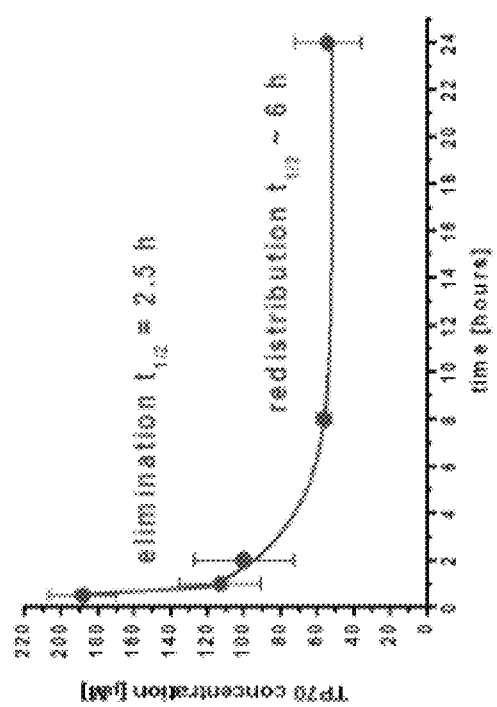

The log P values of CP2 and TP70, determined by octanol/water partition, are 2.20 and 1.90, respectively, suggesting that these compounds can enter the brain. HPLC/mass spectrometry were employed to quantify CP2 and TP70 in the plasma and brain after i.v. administration in mice. The CP2 concentration was 200-300 μM in the mouse brain between 0.5 and 2 h following 25 mg/kg i.v. administration (FIG. 3A). Similarly, TP70 concentration reached 190 μM in plasma at 5 min and 160 μM in brain at 2 h following 25 mg/Kg i.v. administration (FIGS. 3A and 3B). These data indicate CP2 and TP70 have good CNS penetration and can reach therapeutic brain drug concentrations.

Figure 4:
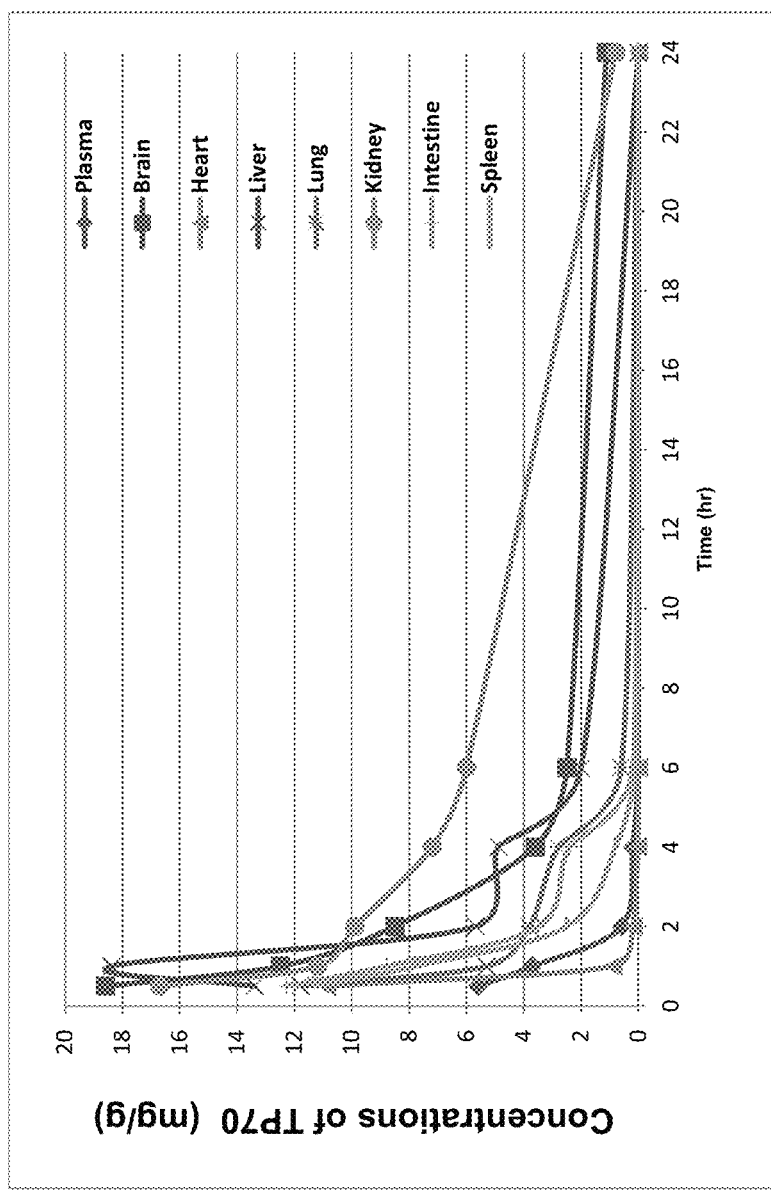
FIG. 4. Concentrations or content of TP70 in the plasma and 7 key organs following ip administration of TP70 (25 mg/kg) in mice (n=3 each data point).

In addition to determination of drug concentrations in plasma and the brain, drug content in other six key organs, the heart, liver, lungs, intestine, and kidneys of mice (male C57BL/6, 3 months, Harlan, n=3 per timepoint) were also assessed in a separate pharmacokinetic (PK) study of TP70 (25 mg/kg, ip,) using HPLC and mass spectrometry. This new PK study confirms that TP70 has higher distribution in the brain than in the plasma and all other organs examined, except for kidneys (FIG. 4). The low distribution in intestines and highest disposition in the kidneys two hours post dosing suggest that the compound might principally be eliminated in original form from kidneys and urinary tract. The lowest distribution in the heart implies there might be low cardiac liability.

Figure 5:
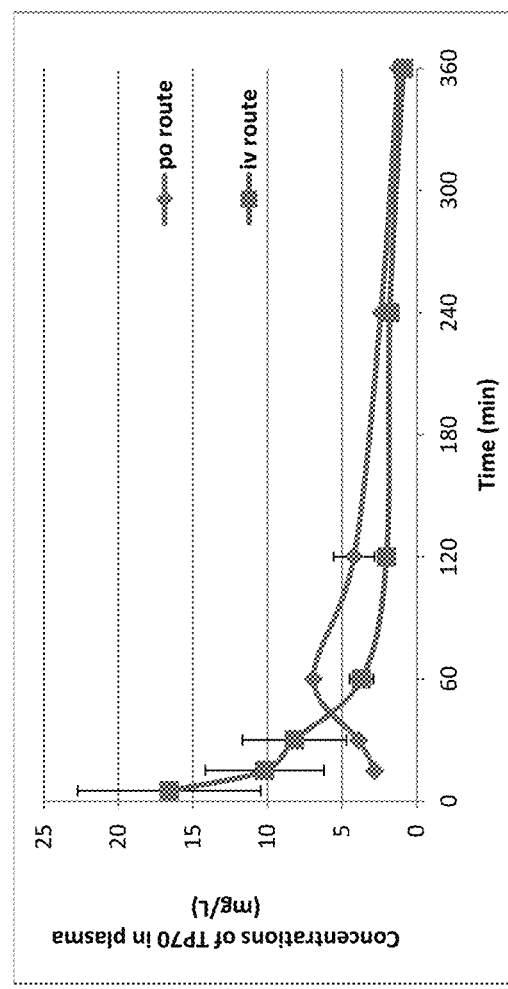
FIG. 5. Plasma concentrations of TP70 following iv or po administration (25 mg/Kg; iv, n=3 in each timepoint; or po, n=3 in each timepoint). Plasma concentrations were plotted against time post-dosing.
Figure 6A:
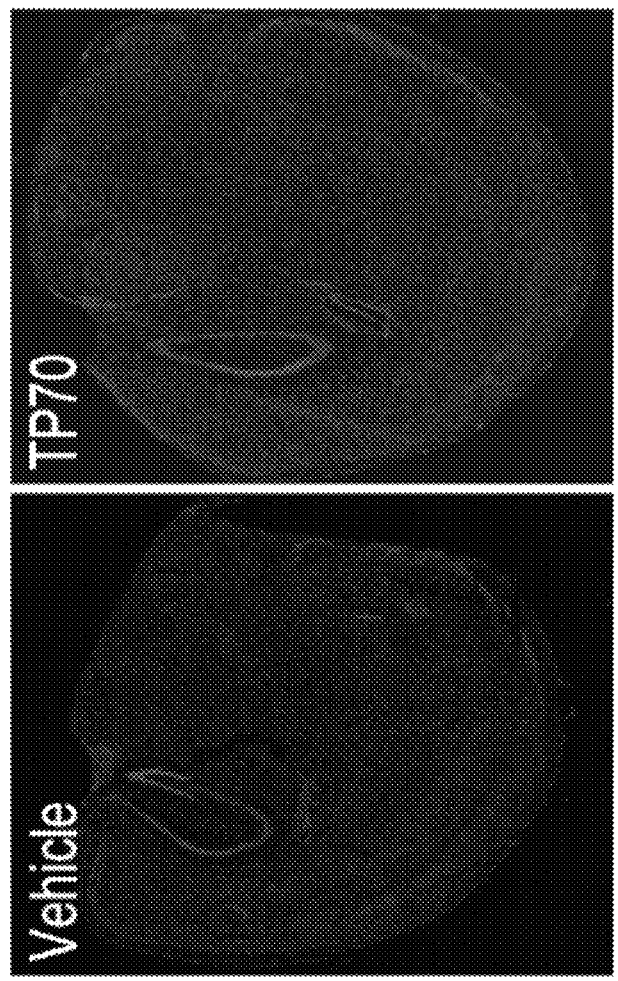
Figure 6C:
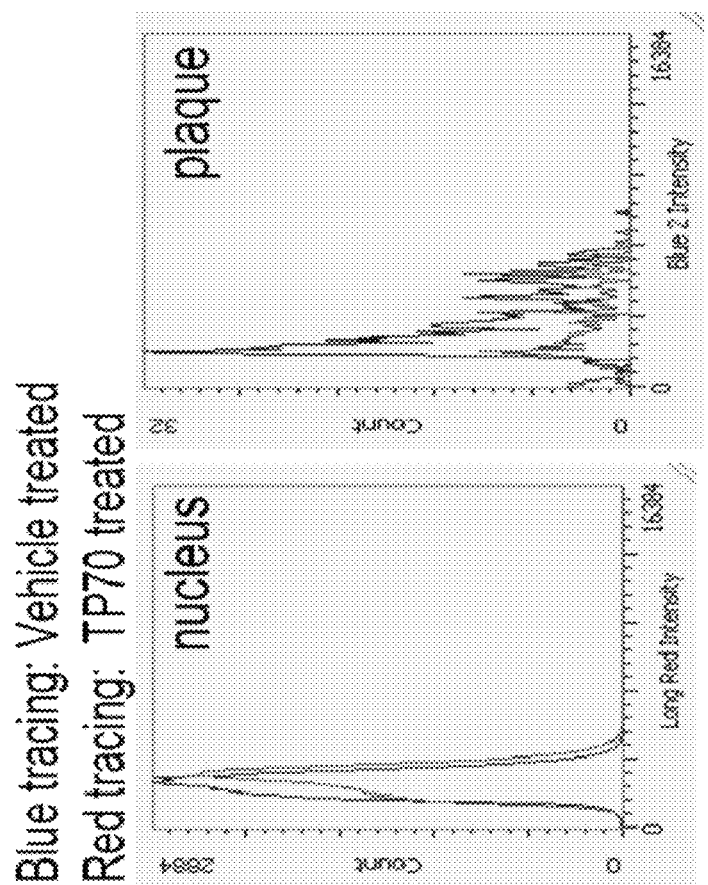
Figure 6D:
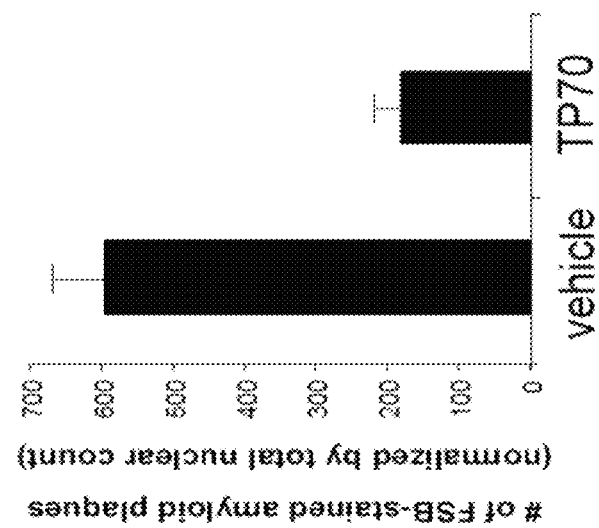
Figure 6E:
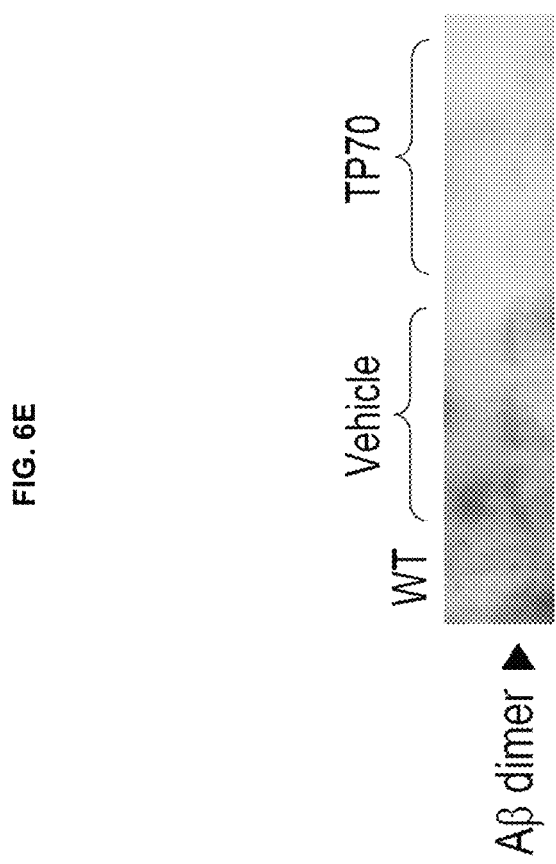

Since the drug will ultimately be administered orally, the bioavailability (F) of TP70 was determined in mice (male C57BL/6, 4 to 6 months old, n=3/group). Each mouse was treated with TP 70 (25 mg/kg). The drug was initially dissolved in pure dimethyl sulfoxide (DMSO) and then diluted with 0.5% hydroxypropylcellulose (HPC) in distilled water in a final solution containing 2% DMSO. At different time points about 50 μl plasma was sampled via tail cut for blood collection with a tube treated with ethylenediaminetetraacetic acid (EDTA). The compound was measured using HPLC/mass spectrometer. The maximal plasma concentration following iv administration is 16.6±6.1 μg/ml (equivalent to 42 μM) and po is 6.9±0.17 μg/ml (equivalent to 17 μM). The t$_{1/2}$ values following drug administration are around 30 min and 160 min for iv and po, respectively. Areas under the curves (AUC) are 989 and 678 for iv and po, respectively. The bioavailability (F) is estimated at 68%. The plasma concentration of TP70 at different timepoints following drug administration are displayed in the Table 1 and were plotted against time post-drug administration as shown in FIG. 5.

TABLE 1

Plasma concentrations of TP70 (25 mg/Kg) in male C57BL/6 mice (~25 g), iv route; n = 3, and po route; n = 3.

| Time (min) | Average concentration of TP70 in plasma (mg/L) | |
|---|---|---|
| | iv route | Oral gavage (po) route |
| 5 | 16.6 ± 6.1 | |
| 15 | 10.2 ± 4 | 2.8 ± 0.09 |

TABLE 1-continued

Plasma concentrations of TP70 (25 mg/Kg) in male
C57BL/6 mice (~25 g), iv route; n = 3,
and po route; n = 3.

| Time (min) | Average concentration of TP70 in plasma (mg/L) | |
|---|---|---|
| | iv route | Oral gavage (po) route |
| 30 | 8.2 ± 3.5 | 3.9 ± 0.14 |
| 60 | 3.7 ± 0.8 | 6.9 ± 0.17 |
| 120 | 2.02 ± 0.6 | 4.2 ± 0.19 |
| 240 | 1.8 ± 0.5 | 2.4 ± 1.37 |
| 360 | 0.9 ± 0.3 | 1.2 ± 0.23 |
| AUC | 989 | 678 |
| F | 1 | 0.68 |

Example 5

In Vivo Efficacy of CP2 and TP70 in 5×—FAD Mice

Although the mechanism of neuron loss in Alzheimer's disease (AD) remains elusive, it is associated with cerebral accumulation of Aβ42. The 5×FAD mouse model of amyloid deposition expresses five familial AD (FAD) mutations that are additive in driving Aβ42 overproduction. 5×FAD mice exhibit intraneuronal Aβ42 accumulation at 1.5 months, amyloid deposition at 2 months, and memory deficits by 4 months of age. We have reported the ability of CP2 to reduce soluble and insoluble Aβ aggregates in vivo (Hong, et al., *J Neurochem*, 2009, 108:1097-1108). After finding that CP2 and TP70 were able to reach potentially therapeutic brain concentrations, we further demonstrated that both compounds were able to substantially reduce cerebral amyloid load and levels of toxic Aβ dimers. As an example, FIG. 6 shows the results from an oral trial of TP70. Since Aβ dimer has been shown to cause memory deficits in rodents (Shankar, et al., *Nat Med*, 2008, 14:837-842) and is the main species of soluble Aβ oligomers in 5×FAD mice (Hong, et al., *Neurobiol Aging*, 2010, 31:1690-1699), the reduction of Aβ dimer by TP70 could lead to improvement in memory. Notably, no apparent drug toxicity was observed during the courses of CP2 or TP70 treatment. No abnormalities in histopathology, hematological counts, and blood chemistry were found at necropsy of the mice.

Example 6

Effects of TP70 on Neurobehavior and Muscle Coordination

Figure 7:
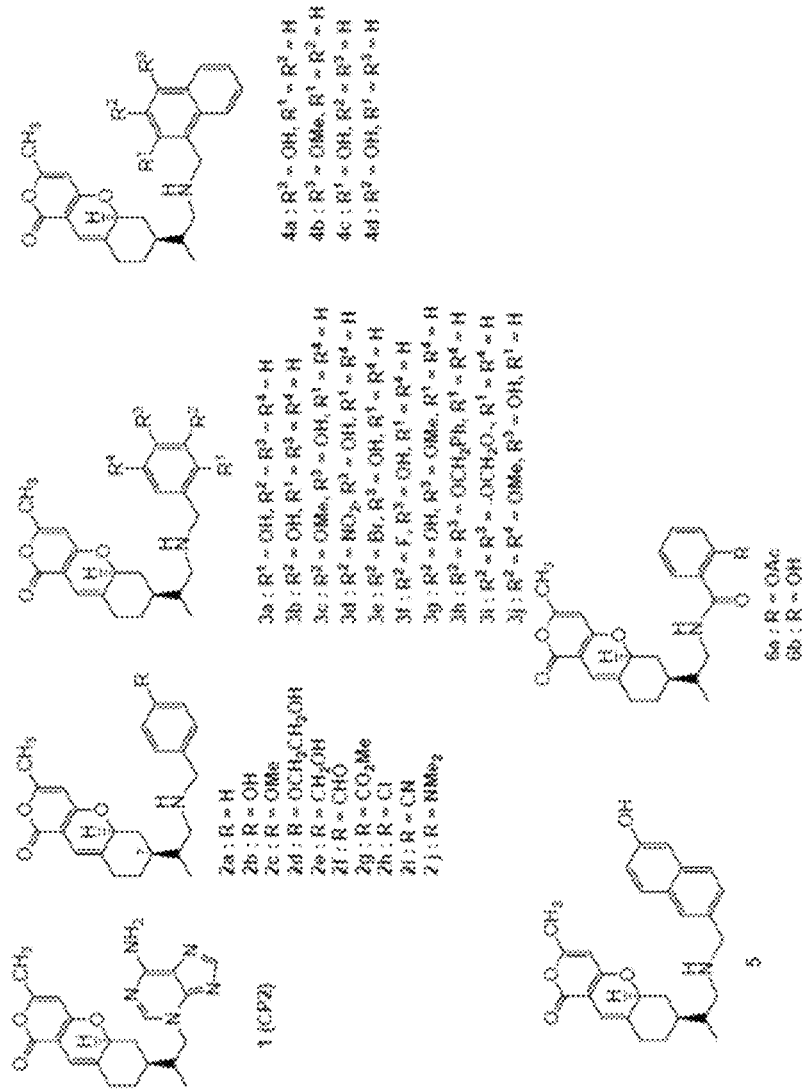
FIG. 7. Synthesized and bioevaluated tricyclic pyrone compounds 1-6 using MC65 cells.
Figure 8A:
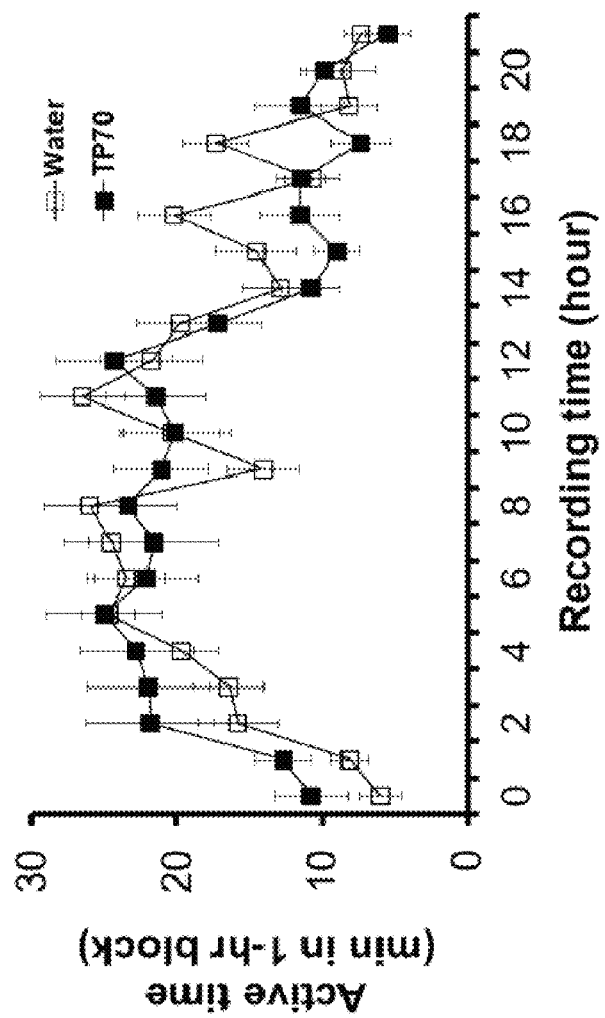
FIGS. 8A-8D. Effects of TP70 on homecage activity and locomotion in homecage monitored using the SmartCage™ system A. Active time in each time block during 24 hours. B. Travel distance in each time block during 24 hours. C. Travel speed in each time block during 24 hours. D. Rearing activity in each time block during 24 hours. The gray shadow indicates dark phase of a 12:12 light/dark cycle.
Figure 8B:
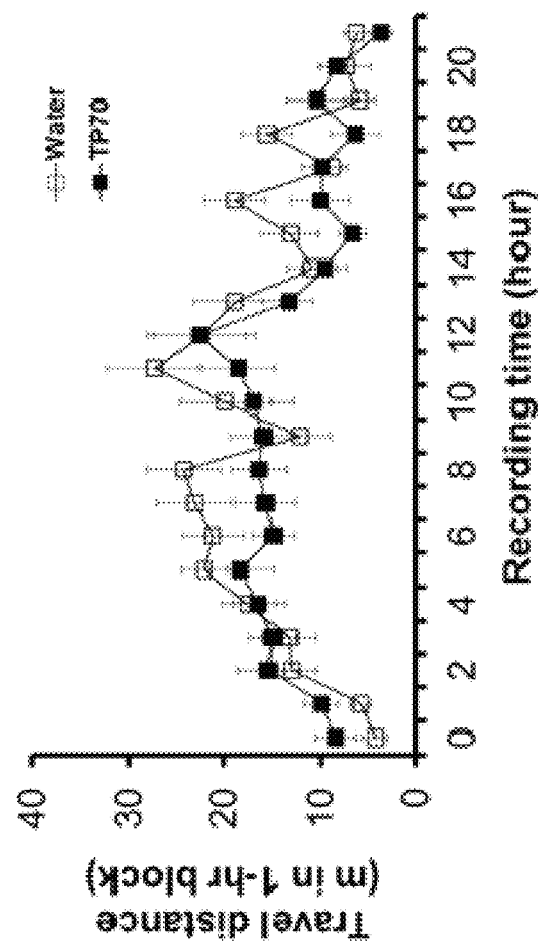
Figure 8C:
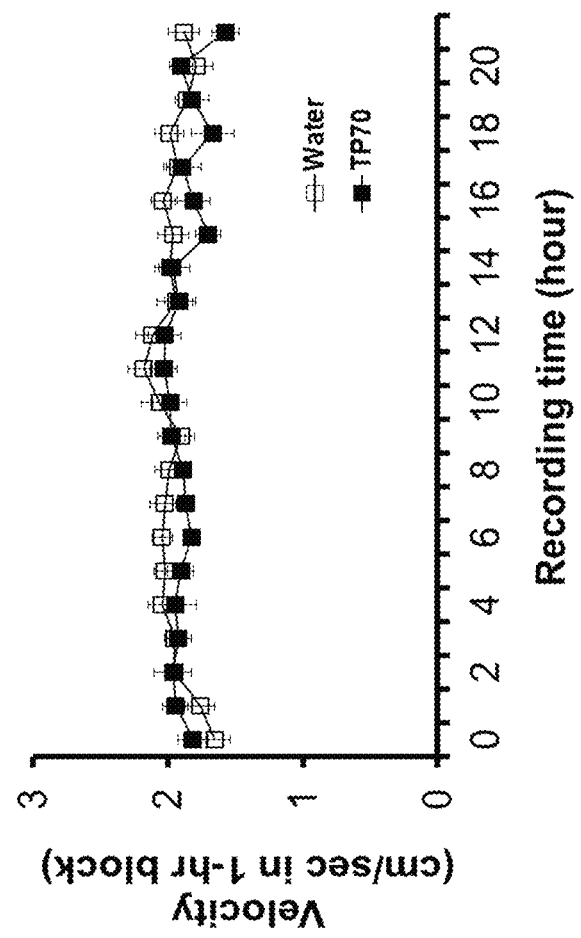
Figure 8D:
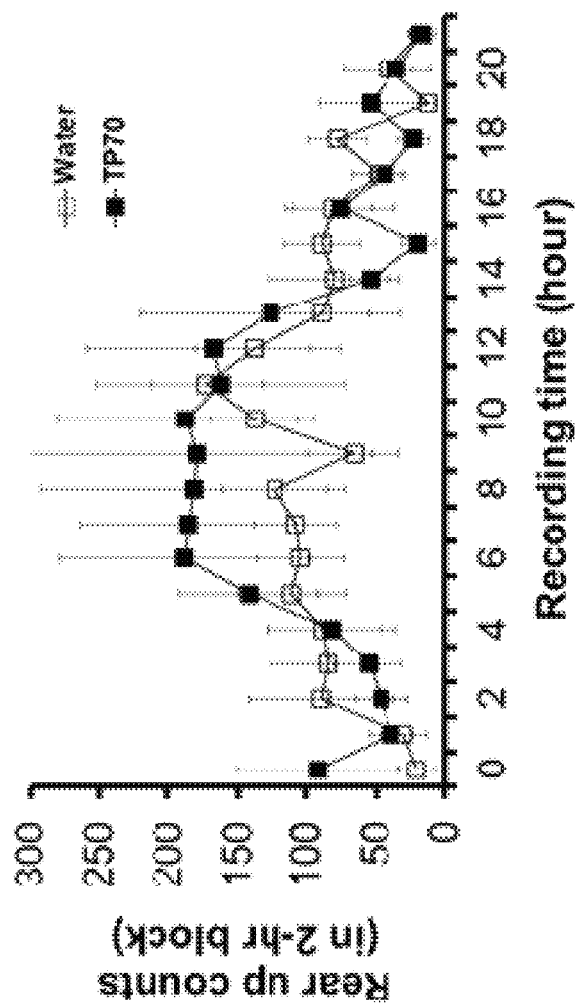
Figure 9:
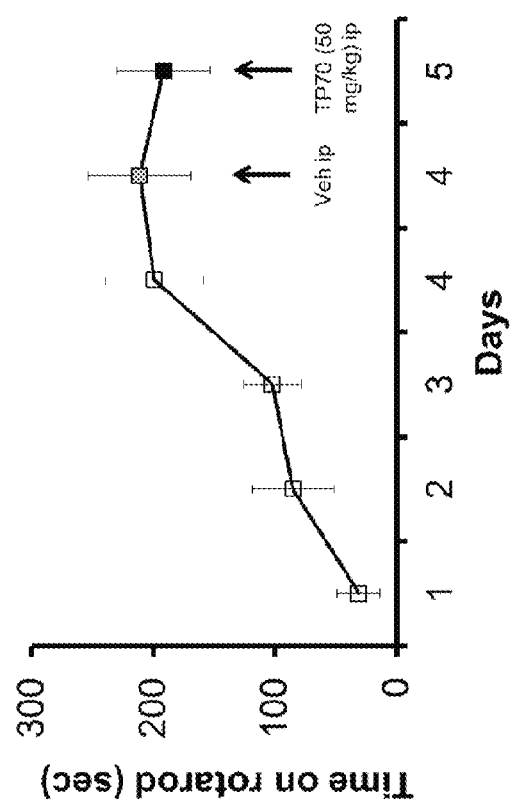
FIG. 9. Effects of TP70 on mouse rotarod performance. The mice were trained three times every day for 4 days to reach its maximal performance using SmartCage Rotarod device (with a setting of a constant speed at 15 resolutions per minute).

The validated SmartCage™ system that enables automated, objective, quantitative and long-term evaluation of neuropsychological endpoints at the animal's home cages (Flores, et al., *IEEE Trans Biomed Eng*, 2007, 54:225-233; Xiong, et al., *Stroke*, 2011, 42:2026-2032; Carter, et al., *Nat Neurosci*, 2010, 13:1526-1533; Khroyan, et al., *Clin Exp Pharmacol Physiol*, 2012, 39:614-622) was used to complement other special individual learning and memory tests (Shineman, et al., *Alzheimers Res Ther*, 2011, 3:28; Hamann, et al., *Neuropsychologia*, 2002, 40:1187-1195; Aultman, et al., *Psychopharmacology* (Berl), 2001, 153:353-364; Ashe, K H, *J Alzheimers Dis*, 2006, 9:123-126). The SmartCage was able to reveal the behavioral phenotypes of a mouse stroke model of middle cerebral artery occlusion (MCAO) (Xiong, et al., *Stroke*, 2011, 42:2026-2032) and a hypocretin/orexin neuron degeneration model (orexin/ataxin-3) (Xie, et al., *J Clin Invest*, 2008, 118:2471-2481; Aultman, et al., *Psychopharmacology* (Berl), 2001, 153:353-364; Hara, et al., *Neuron* 2001, 30:345-354). Compared to sham or wild-type, both MCAO and orexin/ataxin-3 (AT) models displayed neurobehavioral abnormalities (e.g., reduction in locomotion and motor coordination). These validated protocols were applied to PK/PD studies on TP70 in one more AD transgenic model, APP/PS1 mice, which express mutant APPs in combination with mutant PS1. The male APP/PS1 (10-12 months old) mice were group housed in cages consisting of 3-4 mice per cage. Before the treatment of TP70 150-200 uL of blood withdrawn from the tail vein of each mouse. The baseline blood was centrifuged for 15 min @ 5,000 rpm to yield plasma. Plasma was collected and temporally stored in a −20° C. freezer. Each homecage was supplied with a bottle of tap water in the control group or with water containing TP70 (70.7 mg TP70 directly dissolved in 504 mL water) in the treatment group. Mice were allowed to drink water or the TP70 solution freely. By the end of 7 days treatment, weighting the remaining water/solution indicates that approximately averaged 6 ml/day was taken per mouse, consistent with normal mouse daily drinking amount (5-6 ml). By calculation it was estimated 25 mg/day TP70 was taken in per mouse in the treatment group. Homecage activity and locomotion were assessed on Day 7 after the treatment and the blood samples were collected from each mouse after the assessment of general behavior. As shown in FIG. 7, there are no significant differences in homecage activity and locomotion between treatment and control groups. However, the plasma TP70 concentration in the treatment group reached as high as 1.7±0.5 mg/L, equivalent to is 4.3 µM. These plasma expose levels should reach cellular actions required concentrations (cell toxicity protection at submicromolar, and enhancing synaptic activity and LTP restoration at 0.1-3 µM).

To further assess side effects on motor activity, and particularly balance and muscle coordination, rotarod performance was conducted by the wildtype mice (C57BL/6 female, 2 months old, n=7). Vehicle injection (i.p) was given after the Day 4 training to assess any effects of vehicle or injection per se. On Day 5, one hour after TP70 (50 mg/kg, ip) the mice were subject to the rotarod test. As FIG. 8 shows, mice learned to stay on the rotating rod as indicated by gradually increases in time on the rotarod. Vehicle injection did not interfere with the performance on Day 4 and TP70 produced insignificant effects on the rotarod performance.

REFERENCES

1. Galimberti D, Scarpini E. Progress in Alzheimer's disease. J Neurol 2012; 259:201-211.
2. Jin L W, Hearn M G, Ogburn C E, et al. Transgenic mice over-expressing the C-99 fragment of betaPP with an alpha-secretase site mutation develop a myopathy similar to human inclusion body myositis. Am J Pathol 1998; 153:1679-1686.
3. Jin L W, Hua D H, Shie F S, Maezawa I, Sopher B, Martin G M. Novel tricyclic pyrone compounds prevent intracellular APP C99-induced cell death. J Mol Neurosci 2002; 19:57-61.
4. Maezawa I, Zimin P I, Wulff H, Jin L W. Amyloid-beta protein oligomer at low nanomolar concentrations activates microglia and induces microglial neurotoxicity. J Biol Chem 2011; 286:3693-3706.
5. Hong H S, Maezawa I, Budamagunta M, et al. Candidate anti-A beta fluorene compounds selected from analogs of amyloid imaging agents. Neurobiol Aging 2010; 31:1690-1699.

6. Salomone S, Caraci F, Leggio G M, Fedotova J, Drago F. New pharmacological strategies for treatment of Alzheimer's disease: focus on disease modifying drugs. Br J Clin Pharmacol 2012; 73:504-517.
7. Maezawa I, Hong H S, Wu H C, et al. A novel tricyclic pyrone compound ameliorates cell death associated with intracellular amyloid-beta oligomeric complexes. J Neurochem 2006; 98:57-67.
8. Hong H S, Maezawa I, Yao N, et al. Combining the rapid MTT formazan exocytosis assay and the MC65 protection assay led to the discovery of carbazole analogs as small molecule inhibitors of Abeta oligomer-induced cytotoxicity. Brain Res 2007; 1130:223-234.
9. Hong H S, Rana S, Barrigan L, et al. Inhibition of Alzheimer's amyloid toxicity with a tricyclic pyrone molecule in vitro and in vivo. J Neurochem 2009; 108: 1097-1108.
10. Lawlor P A, Bland R J, Das P, et al. Novel rat Alzheimer's disease models based on AAV-mediated gene transfer to selectively increase hippocampal Abeta levels. Mol Neurodegener 2007; 2:11.
11. Hardy J, Selkoe D J. The amyloid hypothesis of Alzheimer's disease: progress and problems on the road to therapeutics. Science 2002; 297:353-356.
12. Klyubin I, Betts V, Welzel A T, et al. Amyloid beta protein dimer-containing human CSF disrupts synaptic plasticity: prevention by systemic passive immunization. J Neurosci 2008; 28:4231-4237.
13. Shankar G M, Li S, Mehta T H, et al. Amyloid-beta protein dimers isolated directly from Alzheimer's brains impair synaptic plasticity and memory. Nat Med 2008; 14:837-842.
14. Lesne S, Koh M T, Kotilinek L, et al. A specific amyloid-beta protein assembly in the brain impairs memory. Nature 2006; 440:352-357.
15. Walsh D M, Klyubin I, Fadeeva T V, Rowan M J, Selkoe D J. Amyloid-beta oligomers: their production, toxicity and therapeutic inhibition. Biochem Soc Trans 2002; 30:552-557.
16. Josien H. Recent advances in the development of gamma-secretase inhibitors. Curr Opin Drug Discov Devel 2002; 5:513-525.
17. Thompson L A, Liauw A Y, Ramanjulu M M, et al. Synthesis and evaluation of succinoyl-caprolactam gamma-secretase inhibitors. Bioorg Med Chem Lett 2006; 16:2357-2363.
18. Ghosh A K, Kumaragurubaran N, Hong L, Koelsh G, Tang J. Memapsin 2 (beta-secretase) inhibitors: drug development. Curr Alzheimer Res 2008; 5:121-131.
19. Olson R E M, L. R. Secretase inhibitors and modulators for the treatment of Alzheimer's disease. Ann Rep Med Chem 2007; 42:27-47.
20. Youm J W, Jeon J H, Kim H, Kim Y H, Ko K, Joung H. Transgenic tomatoes expressing human beta-amyloid for use as a vaccine against Alzheimer's disease. Biotechnol Lett 2008; 30:1839-1845.
21. Cao C, Lin X, Wahi M M, Jackson E A, Potter H, Jr. Successful adjuvant-free vaccination of BALB/c mice with mutated amyloid beta peptides. BMC Neurosci 2008; 9:25.
22. Walsh D M, Townsend M, Podlisny M B, et al. Certain inhibitors of synthetic amyloid beta-peptide (Abeta) fibrillogenesis block oligomerization of natural Abeta and thereby rescue long-term potentiation. J Neurosci 2005; 25:2455-2462.
23. Blanchard B J, Chen A, Rozeboom L M, Stafford K A, Weigele P, Ingram V M. Efficient reversal of Alzheimer's disease fibril formation and elimination of neurotoxicity by a small molecule. Proc Natl Acad Sci USA 2004; 101:14326-14332.
24. Thomas T, Nadackal T G, Thomas K. Aspirin and non-steroidal anti-inflammatory drugs inhibit amyloid-beta aggregation. Neuroreport 2001; 12:3263-3267.
25. Lleo A, Berezovska O, Herl L, et al. Nonsteroidal anti-inflammatory drugs lower Abeta42 and change presenilin 1 conformation. Nat Med 2004; 10:1065-1066.
26. De Felice F G, Wu D, Lambert M P, et al. Alzheimer's disease-type neuronal tau hyperphosphorylation induced by A beta oligomers. Neurobiol Aging 2008; 29:1334-1347.
27. Yang F, Lim G P, Begum A N, et al. Curcumin inhibits formation of amyloid beta oligomers and fibrils, binds plaques, and reduces amyloid in vivo. J Biol Chem 2005; 280:5892-5901.
28. Cheng Y, Feng Z, Zhang Q Z, Zhang J T. Beneficial effects of melatonin in experimental models of Alzheimer disease. Acta Pharmacol Sin 2006; 27:129-139.
29. Dickey C A, Petrucelli L. Current strategies for the treatment of Alzheimer's disease and other tauopathies. Expert Opin Ther Targets 2006; 10:665-676.
30. Adlard P A, Cherny R A, Finkelstein D I, et al. Rapid restoration of cognition in Alzheimer's transgenic mice with 8-hydroxy quinoline analogs is associated with decreased interstitial Ab eta. Neuron 2008; 59:43-55.
31. Quadros A A, L.; Patel, N.; Volmar, C.-H. Relevance of COX-2 inhibitors in Alzheimer's disease. Alzheimer Dis Res J 2007; 1:13-26.
32. Bales K R. Paroxetine administration decreases A D-like pathology and reverses memory impairments in a transgenic model of Alzheimer disease. Exp Neurol 2007; 207:1-3.
33. Rana S, Hong H S, Barrigan L, Jin L W, Hua D H. Syntheses of tricyclic pyrones and pyridinones and protection of Abeta-peptide induced MC65 neuronal cell death. Bioorg Med Chem Lett 2009; 19:670-674.
34. Trushina E, Rana S, McMurray C T, Hua D H. Tricyclic pyrone compounds prevent aggregation and reverse cellular phenotypes caused by expression of mutant huntingtin protein in striatal neurons. BMC Neurosci 2009:10:73.
35. Hua D H, Huang X, Tamura M, et al. Syntheses and bioactivities of tricyclic pyrones. Tetrahedron 2003; 59:4795-4803.
36. Hua D H, Chen Y, Sin H S, et al. A one-pot condensation of pyrones and enals. Synthesis of 1H,7H-5a,6,8,9-tetrahydro-1-oxopyrano[4,3-b][1]benzopyrans. Journal of Organic Chemistry 1997; 62:6888-6896.
37. Hua D H, Chen Y, Sin H S, et al. 6,7,8,9-Tetrahydro-3-methyl-1H-pyrano[4,3-b]quinolin-1-one. Acta Crystallographica Section C-Crystal Structure Communications 1999; 55:1698-1701.
38. Hua D H, Chen Y, Robinson P D, Meyers C Y. (5aS,7S)-7-Isopropenyl-3-methyl-1H,7H-5a,6,8,9-tetrahydro-1-oxopyrano[4,3-b][1]benzopyran. Acta Crystallographica Section C-Crystal Structure Communications 1997; C53:1995-1997.
39. Shineman D W, Basi G S, Bizon J L, et al. Accelerating drug discovery for Alzheimer's disease: best practices for preclinical animal studies. Alzheimers Res Ther 2011; 3:28.
40. Xie X, Wisor J P, Hara J, et al. Hypocretin/orexin and nociceptin/orphanin F Q coordinately regulate analgesia in a mouse model of stress-induced analgesia. J Clin Invest 2008; 118:2471-2481.

41. Hara J, Gerashchenko D, Wisor J P, Sakurai T, Xie X, Kilduff T S. Thyrotropin-releasing hormone increases behavioral arousal through modulation of hypocretin/orexin neurons. J Neurosci 2009; 29:3705-3714.
42. Flores A E, Flores J E, Deshpande H, et al. Pattern recognition of sleep in rodents using piezoelectric signals generated by gross body movements. IEEE Trans Biomed Eng 2007; 54:225-233.
43. Xiong X, Barreto G E, Xu L, Ouyang Y B, Xie X, Giffard R G. Increased brain injury and worsened neurological outcome in interleukin-4 knockout mice after transient focal cerebral ischemia. Stroke 2011; 42:2026-2032.
44. Carter M E, Yizhar O, Chikahisa S, et al Tuning arousal with optogenetic modulation of locus coeruleus neurons. Nat Neurosci 2010; 13:1526-1533.
45. Khroyan T V, Zhang J, Yang L, et al. Rodent motor and neuropsychological behaviour measured in home cages using the integrated modular platform SmartCage( ) Clin Exp Pharmacol Physiol 2012; 39:614-622.
46. Gerashchenko D, Horvath T L, Xie X S. Direct inhibition of hypocretin/orexin neurons in the lateral hypothalamus by nociceptin/orphanin F Q blocks stress-induced analgesia in rats. Neuropharmacology 2011; 60:543-549.
47. Xie X, Crowder T L, Yamanaka A, et al. GABA(B) receptor-mediated modulation of hypocretin/orexin neurones in mouse hypothalamus. J Physiol 2006; 574:399-414.
48. Villeda S A, Luo J, Mosher K I, et al. The ageing systemic milieu negatively regulates neurogenesis and cognitive function. Nature 2011; 477:90-94.
49. Holcomb L, Gordon M N, McGowan E, et al. Accelerated Alzheimer-type phenotype in transgenic mice carrying both mutant amyloid precursor protein and presenilin 1 transgenes. Nat Med 1998; 4:97-100.
50. Hamann S, Monarch E S, Goldstein F C. Impaired fear conditioning in Alzheimer's disease. Neuropsychologia 2002; 40:1187-1195.
51. Aultman J M, Moghaddam B. Distinct contributions of glutamate and dopamine receptors to temporal aspects of rodent working memory using a clinically relevant task. Psychopharmacology (Berl) 2001; 153:353-364.
52. Ashe K H. Molecular basis of memory loss in the Tg2576 mouse model of Alzheimer's disease. J Alzheimers Dis 2006; 9:123-126.
53. Hara J, Beuckmann C T, Nambu T, et al. Genetic ablation of orexin neurons in mice results in narcolepsy, hypophagia, and obesity. Neuron 2001; 30:345-354.
54. Kim W S, Chan S L, Hill A F, Guillemin G J, Garner B. Impact of 27-hydroxycholesterol on amyloid-beta peptide production and ATP-binding cassette transporter expression in primary human neurons. J Alzheimers Dis 2009; 16:121-131.
55. Xie X, Smart T G. Modulation of long-term potentiation in rat hippocampal pyramidal neurons by zinc. Pflugers Arch 1994; 427:481-486.
56. Kamath A V, Wang J, Lee F Y, Marathe P H. Preclinical pharmacokinetics and in vitro metabolism of dasatinib (BMS-354825): a potent oral multi-targeted kinase inhibitor against SRC and BCR-ABL. Cancer Chemother Pharmacol 2008; 61:365-376.
57. Xie X, Steiner S H, Bickel M H. Kinetics of distribution and adipose tissue storage as a function of lipophilicity and chemical structure. II. Benzodiazepines. Drug Metab Dispos 1991; 19:15-19.
58. Rolls A, Colas D, Adamantidis A, et al. Optogenetic disruption of sleep continuity impairs memory consolidation. Proc Natl Acad Sci USA 2011; 108:13305-13310.
59. Roberson E D. Alzheimer's disease and frontotemporal dementia: methods and protocols. New York: Humana Press, 2011.
60. Li J, Liu R, Lam K S, Jin L W, Duan Y. Alzheimer's disease drug candidates stabilize A-beta protein native structure by interacting with the hydrophobic core. Biophys J 2011; 100:1076-1082.
61. Belinson H, Lev D, Masliah E, Michaelson D M. Activation of the amyloid cascade in apolipoprotein E4 transgenic mice induces lysosomal activation and neurodegeneration resulting in marked cognitive deficits. J Neurosci 2008; 28:4690-4701.
62. Maezawa I, Swanberg S, Harvey D, LaSalle J M, Jin L W. Rett syndrome astrocytes are abnormal and spread MeCP2 deficiency through gap junctions. J Neurosci 2009; 29:5051-5061.
63. Song A, Lam, K. S. Parallel solid-phase synthesis of 2-arylamino-6H-pyrano[2,3-f]benzimidazole-6-one. Tetrahedron 2004; 60:8605-8612.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A method for reducing cerebral amyloid load and toxic Aβ dimer level in a subject in need thereof, comprising orally administering to said subject a therapeutically effective amount of a compound of the formula

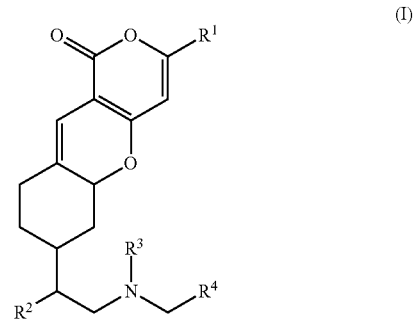

wherein,
$R^1$, $R^2$, and $R^3$ are independently selected from substituted or unsubstituted alkyl and substituted or unsubstituted heteroalkyl; and
$R^4$ is substituted or unsubstituted aryl or substituted or unsubstituted heteroaryl,
wherein $R^4$ is other than adenine joined to the remainder of the compound through an endocyclic nitrogen atom of said adenine,
wherein said therapeutically effective amount is sufficient to achieve therapeutic brain concentration of said compound and reduce cerebral amyloid load and toxic Aβ dimer level, and said compound protects MC65 neuroblastoma cells from death caused by Aβ in a medium-throughput cell-based MC65 protection assay.

2. The method according to claim 1, wherein said compound is of the formula:

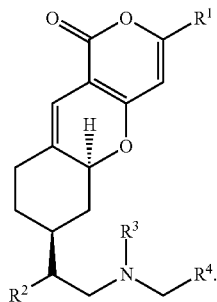

(II)

3. The method according to claim 1, said compound having the structure:

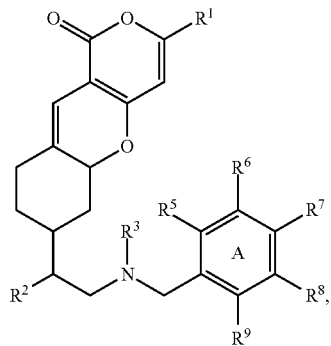

(IV)

wherein $R^5$, $R^6$, $R^7$, $R^8$, and $R^9$ are independently selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^{10}R^{11}$, $-NR^{10}R^{11}$, $-OR^{10}$, $-S(O)_2R^{10}$, $-C(O)R^{10}$, $-COOR^{10}$, $-CONR^{10}R^{11}$, $-S(O)_2OR^{10}$, $-OC(O)R^{10}$, $-C(O)NR^{10}R^{11}$, $-NR^{10}C(O)R^{11}$, $-NR^{10}SO_2R^{11}$ and $-NO_2$, wherein two or more of $R^5$, $R^6$, $R^7$, $R^8$, and $R^9$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl; and $R^{10}$ and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{10}$ and $R^{11}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

4. The method according to claim 3, wherein at least one of $R^5$, $R^6$, $R^7$, $R^8$, and $R^9$ is selected from OH, $C_1$-$C_6$ alkoxy, $C_1$-$C_6$ hydroxyalkyl or a combination thereof.

5. The method according to claim 3, wherein at least one of $R^5$ and $R^6$; $R^6$ and $R^7$; $R^7$ and $R^8$, or $R^8$ and $R^9$, together with the atoms to which they are bonded, are joined to form a phenyl ring, such that moiety A is substituted or unsubstituted napthyl.

6. The method according to claim 3, in which moiety A is napthyl or phenyl, which is substituted with a member selected from OH, $C_1$-$C_6$ alkoxy, $C_1$-$C_6$ hydroxyalkyl or a combination thereof.

7. The method according to claim 1, wherein said compound is a component of a pharmaceutical formulation further comprising a pharmaceutically acceptable carrier.

* * * * *